United States Patent
Kamikake (10) Patent No.: US 10,502,626 B2
(45) Date of Patent: Dec. 10, 2019

(54) FOURIER TRANSFORM TYPE SPECTROPHOTOMETER TO CONTROL A SPEED OF A MOVING MIRROR

(71) Applicant: Shimadzu Corporation, Kyoto (JP)

(72) Inventor: Tadafumi Kamikake, Kyoto (JP)

(73) Assignee: Shimadzu Corporation, Nishinokyo-Kuwabaracho, Nakagyo-ku, Kyoto-shi, Kyoto (JP)

( * ) Notice: Subject to any disclaimer, the term of this patent is extended or adjusted under 35 U.S.C. 154(b) by 0 days.

(21) Appl. No.: 15/558,165

(22) PCT Filed: Mar. 13, 2015

(86) PCT No.: PCT/JP2015/057584
§ 371 (c)(1),
(2) Date: Sep. 13, 2017

(87) PCT Pub. No.: WO2016/147271
PCT Pub. Date: Sep. 22, 2016

(65) Prior Publication Data
US 2018/0073927 A1    Mar. 15, 2018

(51) Int. Cl.
*G01J 3/453* (2006.01)
*G01N 21/27* (2006.01)
(Continued)

(52) U.S. Cl.
CPC ........... *G01J 3/4535* (2013.01); *G01J 3/0202* (2013.01); *G01J 3/027* (2013.01); *G01J 3/0275* (2013.01);
(Continued)

(58) Field of Classification Search
CPC ...... G01J 3/4535; G01J 3/0203; G01J 3/0291; G01J 3/0297; G01J 3/06; G01J 2003/061;
(Continued)

(56) References Cited

U.S. PATENT DOCUMENTS 3,936,193 A    2/1976  Auth
4,662,730 A *  5/1987  Outwater ............. A61B 3/1225
                                                 351/212
(Continued)

FOREIGN PATENT DOCUMENTS

AT    505305 A4    12/2008
EP    0664443 A1    7/1995
(Continued)

OTHER PUBLICATIONS

Extended European Search Report dated Feb. 28, 2018 for the corresponding European Patent Application No. 15885369.7.
Written Opinion for application No. PCT/JP2015/057584.

*Primary Examiner* — Michael P LaPage
(74) *Attorney, Agent, or Firm* — Muir Patent Law, PLLC (57) ABSTRACT

A Fourier transform type spectrophotometer capable of stably controlling a speed of a moving mirror comprises a movable unit to which a moving mirror is fixed, outside-force-applying means configured to apply external force larger than movement resistance of the movable unit to the movable unit, a driving source configured to apply positive or negative driving force along the moving direction of the movable unit to the movable unit, a speed measurement unit configured to measure the speed of the movable unit, and a driving force control unit configured to control the driving force of the driving source so that the movable unit is moved in a predetermined manner based on the speed, wherein a rate of fluctuation of the driving force is suppressed by operating in a state in which the driving force of the driving source is high due to the external force to thereby stabilize the control.

7 Claims, 6 Drawing Sheets

(51) Int. Cl.
  *G01J 3/02* (2006.01)
  *G01J 3/06* (2006.01)
(52) U.S. Cl.
  CPC .............. *G01J 3/0289* (2013.01); *G01J 3/06* (2013.01); *G01N 21/27* (2013.01); *G01J 2003/064* (2013.01)
(58) Field of Classification Search
  CPC .. G01J 2003/062; G01J 2003/064; G01J 3/45; G01N 21/3563
  See application file for complete search history.

(56) References Cited

U.S. PATENT DOCUMENTS

| | | | | |
|---|---|---|---|---|
| 4,991,961 | A * | 2/1991 | Strait | G01J 3/4535 356/452 |
| 5,400,184 | A * | 3/1995 | Kuklo | G02B 7/1827 248/476 |
| 5,671,058 | A * | 9/1997 | Kawaguchi | G01J 3/4535 310/90.5 |
| 6,845,187 | B1 * | 1/2005 | Weaver | H04J 14/0213 385/15 |
| 2008/0315103 | A1 * | 12/2008 | Yamamoto | G01J 3/02 250/339.08 |
| 2013/0222809 | A1 * | 8/2013 | Hara | G01J 3/0208 356/451 |
| 2015/0192464 | A1 * | 7/2015 | Fukuda | G01J 3/4535 356/51 |
| 2016/0084711 | A1 * | 3/2016 | Iwata | G01J 3/4535 356/319 |

FOREIGN PATENT DOCUMENTS

| | | |
|---|---|---|
| JP | 11-211412 | 8/1999 |
| JP | 2009-139352 | 6/2009 |
| JP | 2013-213721 | 10/2013 |

\* cited by examiner

(Prior Art)

FOURIER TRANSFORM TYPE SPECTROPHOTOMETER TO CONTROL A SPEED OF A MOVING MIRROR

TECHNICAL FIELD

The present invention relates to a Fourier transform type spectrophotometer.

BACKGROUND TECHNIQUE

In an FTIR (Fourier Transform Infrared Spectroscope), infrared light from an infrared light source is split into two by a beam splitter, one of them is irradiated to a fixed mirror, the other is irradiated to a moving mirror, and these reflected light is guided to the same optical path again to be interfered. This interference light is irradiated to a sample which is a measurement target, and the transmitted light or the reflected light is detected and subjected to a Fourier transform to create a spectrum. From the peak wavelengths, the peak intensities, etc., of the spectrum, qualitative analyses and quantitative analyses of the sample are performed.

In the FTIR, normally, a control interference system is equipped as an optical system which is different from the aforementioned optical system of measurement light (infrared light) to be irradiated to a sample. The control interference system shares a beam splitter, a fixed mirror, and a moving mirror with the optical system of measurement light and is provided with a laser light source and a laser light detector for the control interference system. The control interference system generates interference light by passing laser light through the same interference system as the measurement light. Based on the interference signal of this laser light, the current position and the speed of the moving mirror are calculated.

The moving mirror is fixed to a movable unit capable of reciprocating on a guide, and the movable unit is driven by a driving motor. When driving force is applied from the driving motor to the movable unit, force which prevents a movement (movement resistance) due to the frictional force, the viscosity resistance of a lubricant, etc., is generated at the sliding portion of the movable unit and a guide portion. Therefore, by changing the voltage of the driving motor, the driving force to the movable unit is changed to adjust the moving speed.

Figure 6:
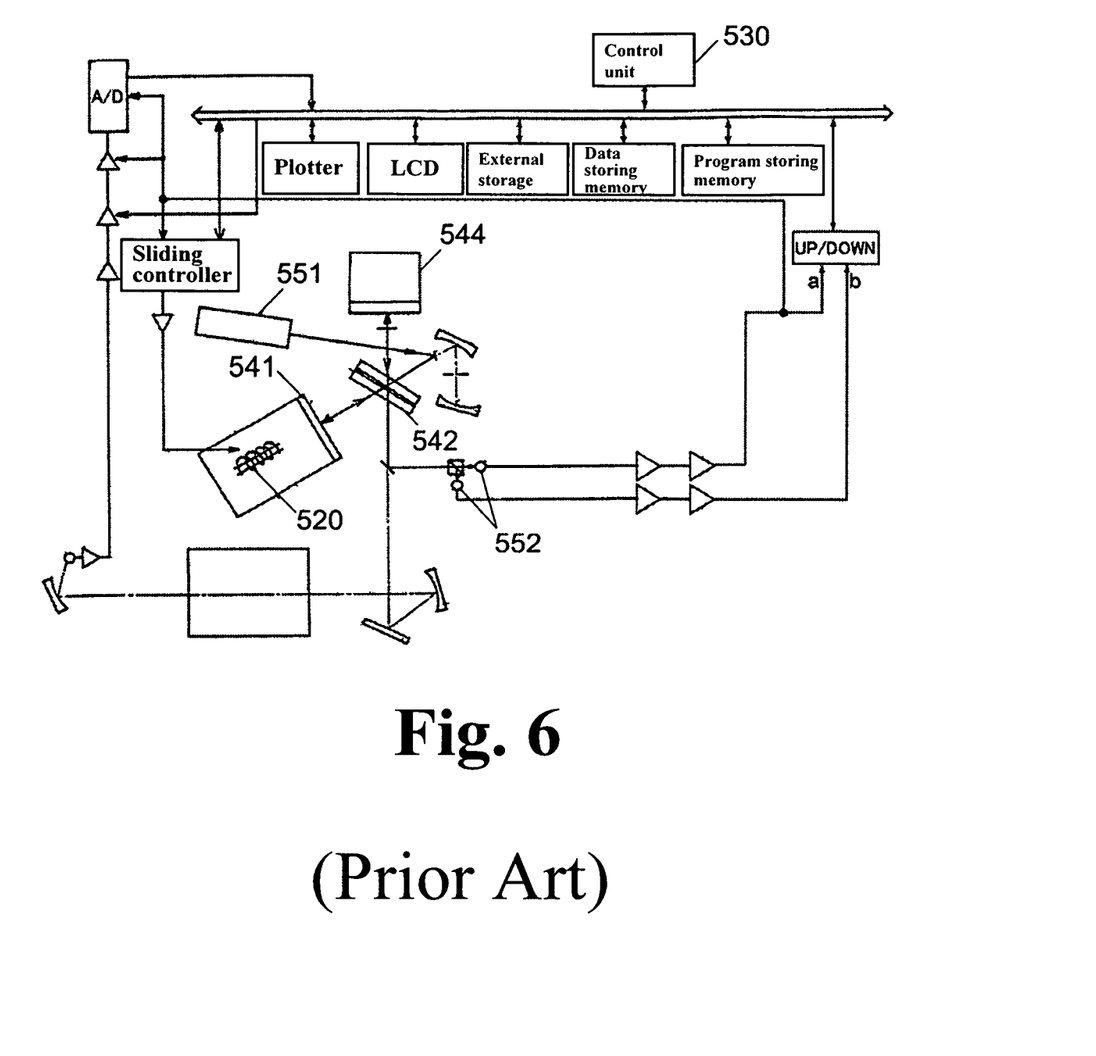
FIG. 6 is a schematic configuration diagram of a Fourier transform infrared spectrophotometer according to a conventional technique.

As a control method of such a moving mirror speed, feedback control is sometimes used as described in Patent Document 1. In Patent Document 1, as shown in FIG. 6, the light from the laser light source 551 is interfered by the moving mirror 541 and the fixed mirror 544, and the intensity of the interference light is measured by the photodiode 552 to thereby calculate the current position and the speed of the moving mirror 541. Then, the control unit 530 applies the driving voltage to the driving motor 520 by feedback control by the PID control (Proportional-Integral-Derivative Control) based on, e.g., the deviation between the measured speed and the target speed, and performs the speed adjustment of the moving mirror 541.

In the case of measuring spectral characteristics of a sample, it is important to acquire accurate spectral data in order to perform accurate measurement. In the FTIR, an output signal is output every time the moving mirror passes through a specific position by the control interference system. During each output position, a detection signal of infrared interference light is accumulated in a detector and taken out as spectral data. Therefore, when the moving mirror is operated at a constant speed, the accumulation time every data becomes even, which enables stable acquisition of spectral data.

PRIOR ART

Patent Document

Patent Document 1: Japanese Unexamined Patent Application Publication No. 2013-213721

SUMMARY OF THE INVENTION

Problems to be Solved by the Invention

The speed of the moving mirror sometimes changes due to the entry of foreign objects such as minute dusts to the sliding portion. When a foreign object is entered to the sliding portion, the movement resistance of the movable unit increases when the movable unit comes into contact with and runs over the foreign object, resulting in a temporal speed reduction of the moving mirror. Then, the difference from the target speed increases, and therefore the control device performing the feedback control increases the driving voltage of the driving motor to try to return the speed of the moving mirror to the target speed. On the other hand, after the movable unit runs over the foreign object, the movement resistance decreases, so that the force from the driving motor becomes larger than the movement resistance, which accelerates the moving mirror. When the speed of the moving mirror exceeds the target speed, the control device lowers the voltage of the driving motor to decelerate the moving mirror.

During that time, in cases where the feedback control cannot cope with such a speed change, there occur problems such that the moving mirror temporarily stops, the control diverges, etc.

When the accumulation time of the detection signal in the detector is lengthened, large signal data can be obtained and spectral data with a high S/N ratio can be obtained. For this reason, in some cases, the moving speed of the moving mirror is set to a low speed. In this case, since the viscous resistance of the lubricant becomes small and the movable unit can be moved with small force, the driving motor is often operated at a low voltage. In such a case, even in cases where a small foreign object is entered to the sliding portion, the amount of change in the voltage with respect to the original voltage becomes relatively large, and therefore the problems of the feedback control described above appear particularly conspicuously.

An object to be solved by the present invention is to provide a Fourier transform type spectrophotometer capable of stably controlling a speed of a moving mirror and performing measurement with high accuracy.

Means For Solving the Problems

A Fourier transform type spectrophotometer according to the present invention made to solve the aforementioned problem includes:

a) a movable unit to which a moving mirror is fixed;

b) outside-force-applying means configured to always apply external force larger than movement resistance of the movable unit to the movable unit;

c) a driving source configured to apply positive or negative driving force along a moving direction of the movable unit to the movable unit;

d) a speed measurement unit configured to measure a moving speed of the movable unit; and e) a driving force control unit configured to control the driving force of the driving source so that the movable unit is moved in a predetermined manner based on the moving speed.

In the Fourier transform type spectrophotometer according to the present invention, the movement resistance, the external force from the outside-force-applying means, and the driving force from the driving source are applied to the movable unit, and the resultant force thereof moves the movable unit. Among them, the external force is larger than the movement resistance. Therefore, in the absence of driving force, the movable unit is always accelerated by the external force. In a conventional Fourier transform type spectrophotometer, since such external force was not applied to the movable unit, the movable unit was in a stopped state by the movement resistance in a normal circumstance.

The driving force control unit adds controlled driving force to the resultant force of the movement resistance and the external force based on the measurement result of the speed measurement unit so that the movement of the movable unit becomes in a predetermined manner. For example, by giving driving force in a direction opposite to the direction of the external force, the resultant force is made zero so that the stationery state of the movable unit is maintained or the movable unit is moved at a constant speed. Alternatively, by increasing or decreasing the driving force from such a zero resultant force state, the movable unit is transitioned from the stationary state to the moving state. Similarly, when the movable unit is in a constant speed movement state, the driving unit is accelerated or decelerated by increasing or decreasing the driving force to thereby, for example, perform a reciprocating motion. In this case, the driving force applied to the movable unit is in some cases directed in the same direction as the movement direction of the movable unit, and in other cases the driving force is directed in a direction opposite to the movement direction of the movable unit. In the former case, the driving force is positive driving force, and in the latter case the driving force is negative driving force.

With such a configuration, the driving force required to move the movable unit at a constant speed becomes larger by the influence of the external force as compared with the driving force of a conventional technique in a part or the entirety of the moving range of the moving mirror. Therefore, even in cases where the moving speed of the movable unit suddenly fluctuates for some reasons, the change amount of the driving force due to the adjustment can be decreased relatively.

Gravity may be used as the outside-force-applying means. This can be accomplished by configuring such that the moving direction of the movable unit is set in the upward and downward direction with respect to the gravity so that the direction of driving force applied by the driving source to the movable unit is in a direction opposite to the gravity. Therefore, the Fourier transform type spectrophotometer according to the present invention made to solve the aforementioned problems includes:

a) a movable unit to which a moving mirror is fixed, the movable unit being movable on a guide;

b) inclination means configured to incline the guide such that component force of gravity of the movable unit in a direction along the guide is greater than movement resistance on the guide of the movable unit;

c) a driving source configured to apply positive or negative driving force along a moving direction of the movable unit on the guide;

d) a speed measurement unit configured to measure a moving speed of the movable unit; and e) a driving force control unit configured to control the driving force of the driving source so that the movable unit is moved on the guide in a predetermined manner based on the moving speed.

In this configuration, since the movable unit is movable on the guide and the guide is inclined, the component force of its own weight (gravity) in a direction along the guide is always applied downward along the guide to the movable unit. This becomes the external force. By changing the inclination angle of the guide, the external force applied to the movable unit can be adjusted.

As other outside-force-applying means, it is also possible to use a configuration in which the movable unit or a movable portion in the driving source is urged by an elastic member. In this configuration, the force applied from the elastic member to the movable unit, etc., becomes the external force. Here, by appropriately selecting the elastic coefficient of the elastic member (for example, in the case of using a spring, the spring constant of the spring used), the external force applied to the movable unit, etc., can be adjusted.

Effects of the Invention

In the Fourier transform type spectrophotometer according to the present invention, the driving force of the driving source is adjusted by adding the external force from the outside-force-applying means to the movable unit. Therefore, even in cases where speed fluctuation occurs due to intrusion of a foreign object, etc., by making the relative change amount with respect to the driving force before the speed fluctuation small in a part or the entirety of the moving range of the moving mirror, feedback control becomes more stable than before, and divergence of control can be suppressed. Also, as feedback control stabilizes, the speed change of the movable unit is reduced. As a result, it becomes easy to keep the speed of the moving mirror at a constant speed, and the device lifetime can be prolonged because abrupt speed change disappears.

BRIEF DESCRIPTION OF THE DRAWINGS

FIG. 2 is a view showing a configuration of a moving mirror and an outside-force-applying means according to a first embodiment, wherein

FIG. 3 is a view showing a configuration of a moving mirror and an outside-force-applying means according to a second embodiment, wherein FIG. 3A is a view showing a state in which extension of a coil spring is large, and wherein

FIG. 4 is a view showing a configuration of a moving mirror and an outside-force-applying means according to a third embodiment, wherein

4B is a view showing a state in which a second coil spring is extended.

FIG. 5 is a view showing a moving mirror and an outside-force-applying means according to a fourth embodiment, wherein

EMBODIMENT FOR CARRYING OUT THE INVENTION

EXAMPLE 1

Figure 1:
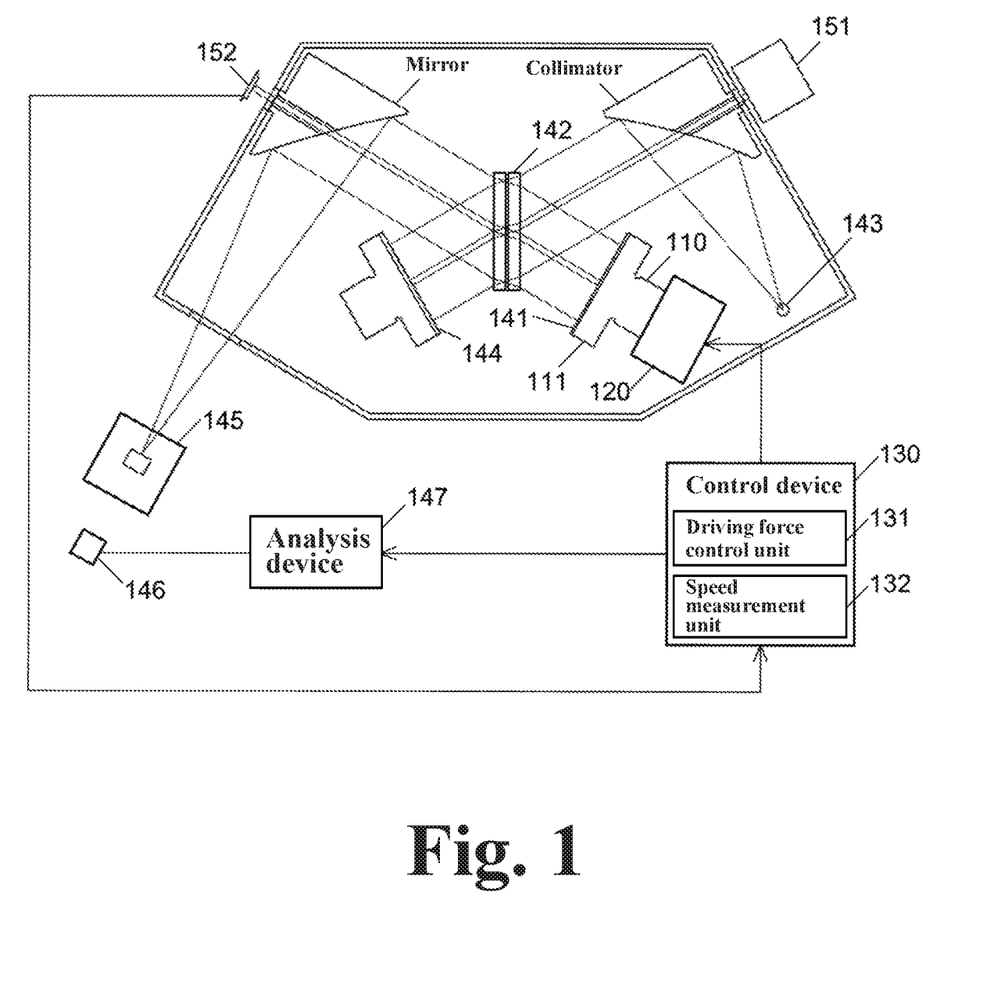
FIG. 1 is a schematic configuration diagram of a Fourier transform infrared spectrophotometer according to the present invention.

Hereinafter, a Fourier transform type spectrophotometer according to a first embodiment of the present invention will be described with reference to FIGS. 1 and 2. In the Fourier transform type spectrophotometer in this embodiment, as shown in FIG. 1, the infrared light from the infrared light source 143 is divided into two by the beam splitter 142 and irradiated to the fixed mirror 144 and the moving mirror 141, and these reflected lights are guided to the same optical path again and made to interfere. This interference light is irradiated to a sample in a sample chamber 145, and the transmitted light is detected by an infrared light detector 146. The detected signal is Fourier transformed by an analysis device 147 to create a spectrum, and an analysis of the sample from the spectral data is performed. Also, the laser light irradiated from the laser light source 151 becomes interference light on the same optical path as the infrared light. The interference light is detected by the laser light detector 152, and the moving speed and the current position of the moving mirror 141 are calculated by the speed measurement unit 132 of the control device 130 based on the detected data. The calculated moving speed and the current position are used to control the driving voltage of the voice coil motor 120 in the driving force control unit 131 of the control device 130 and to create spectral data of the analysis device 147.

The linear motion mechanism 110 is composed of a linear guide 112 and a movable unit 111 reciprocating on the linear guide 112. The moving mirror 141 is fixed to the movable unit 111 so as to move by the voice coil motor 120.

The operation of the Fourier transform type spectrophotometer in this embodiment will be described with reference to FIG. 2. In FIG. 2, only the linear motion mechanism 110, the voice coil motor 120, and the inclination giving portion 160 are depicted. Since the configurations other than the above are the same as those of a conventional technique, the descriptions of these operations will be omitted arbitrarily.

Figure 2A:
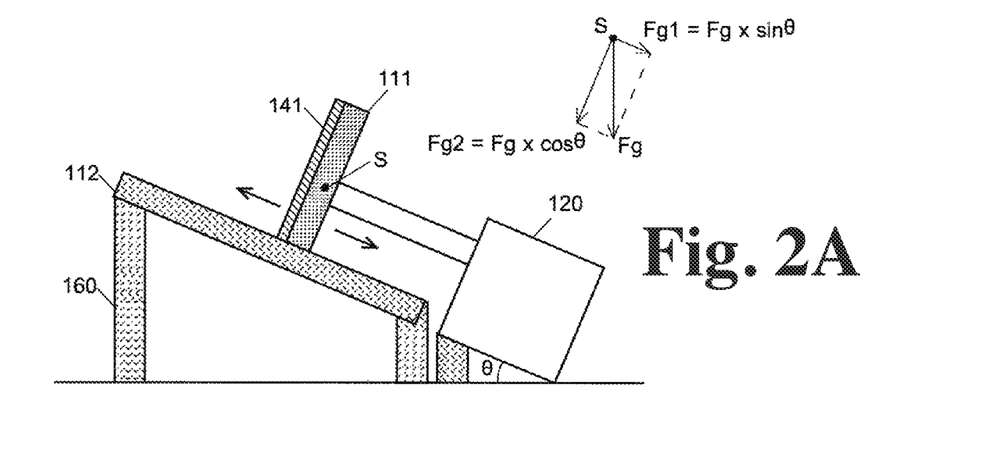
FIG. 2A is a view showing force due to the own weight of the moving mirror.
Figure 2B:
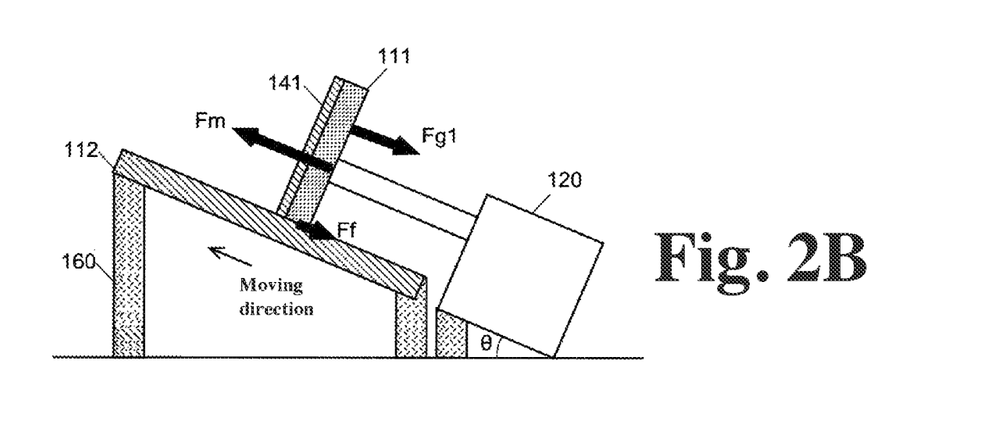
FIG. 2B is a view showing a state in which the moving mirror is moving upward, and FIG. 2C a view showing a state in which the moving mirror is moving downward.
Figure 2C:
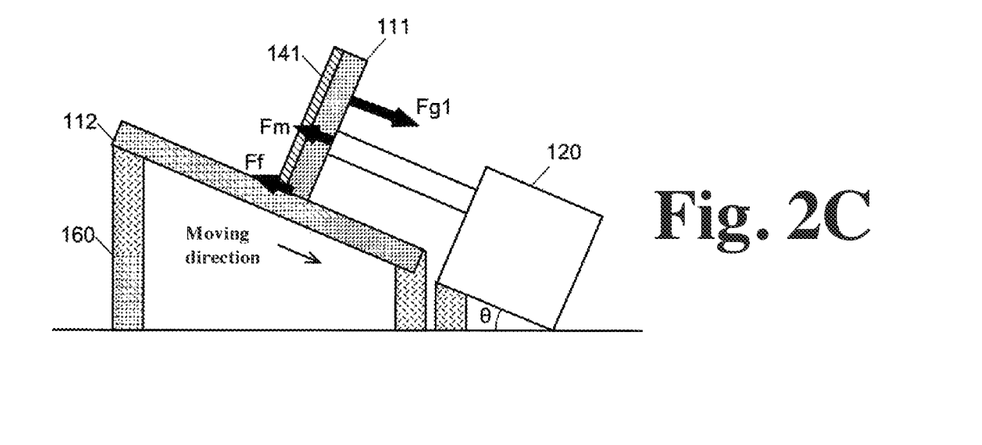

In this embodiment, as shown in FIG. 2A, the linear guide 112 is placed on the inclination giving portion 160 and inclined by 30° with respect to the horizontal direction. Accordingly, the movable unit 111 reciprocates upward and downward along the linear guide 112 with respect to the gravity on the surface inclined by 30° from the horizontal direction. In this embodiment, the inclination is set to 30°. However, depending on the mass of the movable unit 111 and the moving mirror 141, the inclination θ may be appropriately changed in a range from −90° to 90° (excluding 0°).

Although the force (gravity) Fg due to its own weight is applied to the moving mirror 141 and the movable unit 111 in the vertical direction, the linear guide 112 is installed in an inclined manner. Therefore, in the moving direction of the moving mirror 141, according to the inclination θ of the linear guide 112, the component force Fg1 of Fg is always added to the voice coil motor 120.

When the measurement of the spectral characteristic of the sample is started, the driving force control unit 131 applies a voltage to the voice coil motor 120 to move the moving mirror 141. For example, in the case of moving the moving mirror 141 upward with respect to the horizontal direction, as shown in FIG. 2B, the external force Fg1 and the movement resistance Ff are generated. Therefore, by adjusting the driving voltage so that the force Fm applied from the voice coil motor 120 becomes equal to the sum of the aforementioned force, the moving mirror 141 is moved at a constant speed. On the other hand, in the case of moving the moving mirror 141 downward with respect to the horizontal direction, the movement resistance Ff becomes in the opposite direction as shown in FIG. 2C. Therefore, by adjusting the driving voltage so that the force Fm applied from the voice coil motor 120 becomes equal to the difference between Fg1 and Ff, the moving mirror 141 is moved at a constant speed. In this case, the driving force Fm of the voice coil motor becomes smaller than that in the case in which the moving mirror is moved upward. Therefore, in order to always make the driving force Fm from the voice coil motor larger than the driving force Fm' required to move at a constant speed in a conventional technique (in the case of moving in the horizontal direction), it is preferable to provide such inclination so that the external force Fg1 is larger than 2×Ff (Fg1>2×Ff).

In cases where no foreign object is entered to the sliding portion, feedback control can be performed easily since the force applied from the voice coil motor 120 to the movable unit 111 is constant. Further, at both ends of the movable range of the moving mirror 141, it is required to perform deceleration and acceleration for switching the moving direction. However, the voltage change amount thereof is the same as that in a conventional technology, and therefore the control can be performed by feedback control similar to a conventional feedback control.

On the other hand, in cases where a foreign object is entered between the linear guide 112 and the movable unit 111, since the movement resistance of the portion increases, the moving mirror 141 is temporarily decelerated. The speed measurement unit 132 calculates the current speed of the moving mirror 141 from the output signal of the laser interference system 150 and increases the driving voltage to be supplied to the voice coil motor 120 according to the different between the current speed and the target speed.

The increased amount of the driving voltage at this time is the same as that in the case in which the same foreign object is entered to the linear guide 112 set in the horizontal direction as in a conventional case. On the other hand, the driving voltage of the voice coil motor 120 in a state (steady state) in which no foreign object is entered in this embodiment is larger than that in a conventional case. Therefore, the rate of voltage rise at the time of the entry of the foreign object with respect to the driving voltage in the steady state, that is, the rate of fluctuation of the driving voltage becomes smaller than that in a conventional case. As a result, the feedback control becomes more stable than in a conventional case, and therefore the moving mirror 141 can be moved at a constant speed.

By installing the linear guide 112 in an inclined manner as described above, it is possible to add the external force to the moving mirror 141 beforehand and raise the driving voltage of the voice coil motor 120 higher than in a conventional case, so that even in cases where a foreign object is entered, it is possible to stabilize the feedback control. In addition, the external force Fg1 at this time can be adjusted by changing the inclination of the linear guide 112 and the mass of the movable unit 111 or the moving mirror 141.

EXAMPLE 2

Figure 3A:
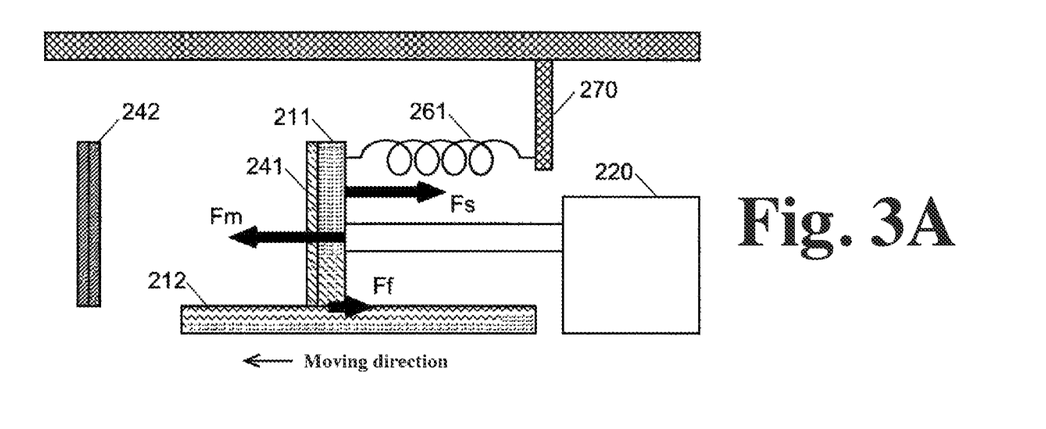
Figure 3B:
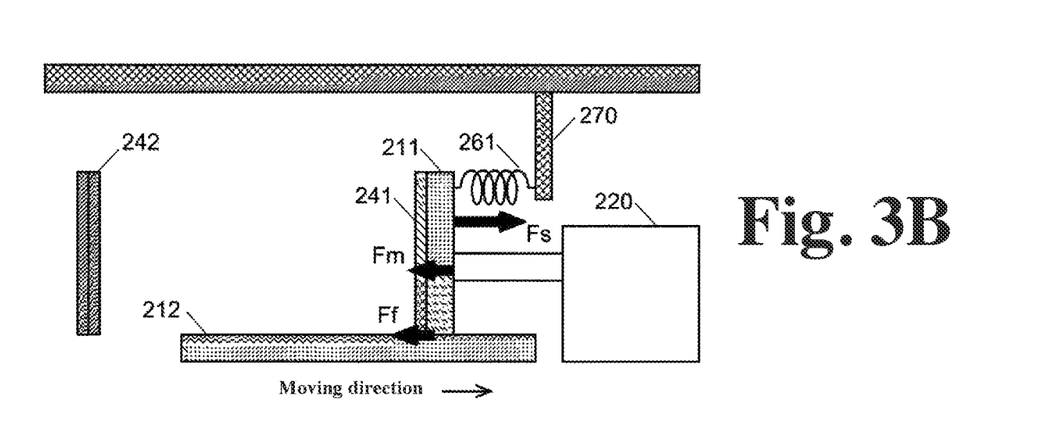
FIG. 3B is a view showing a state in which the extension of the coil spring is small.

Next, a second embodiment will be described with reference to FIG. 3. In this embodiment, as shown in FIG. 3, the linear guide 212 is installed horizontally, and a coil spring 261 is inserted between a movable unit 211 and an elastic member fixing portion 270. Since other configurations are the same as those in the first embodiment, the last two digits of the reference numeral are allotted to the reference numeral in the above embodiment, and the description thereof will be omitted arbitrarily.

The operation of the Fourier transform type spectrophotometer in this embodiment will be described with reference to FIG. 3. The coil spring 261 applies the external force Fs proportional to the spring constant and the extension of the spring to the movable unit 211. Therefore, as shown in FIG. 3A, as the movable unit 211 is closer to the beam splitter 242, the external force Fs due to the coil spring 261 becomes stronger, and as it moves away from the beam splitter 242, the external force Fs becomes weaker as shown in FIGS. 3B. In order to increase the driving force Fm in the present invention as compared with the driving force Fm' required to move the moving mirror at a constant speed in a conventional technology, it is preferable to install the coil spring 261 so that the external force Fs becomes larger than 2×Ff (Fs>2×Ff) by the coil spring 261 in the entire moving range of the moving mirror.

When the measurement of the spectral characteristic of the sample is started, the driving force control unit 231 applies a voltage to the voice coil motor 220 to move the moving mirror 241. For example, in the case of moving the moving mirror 241 in a direction of approaching the beam splitter 242, as shown in FIG. 3A, the external force Fs and the movement resistance Ff are generated. Therefore, the voltage is adjusted so that the force Fm applied from the voice coil motor 220 becomes equal to the sum of the external force Fs and the movement resistance Ff, so that the moving mirror 241 moves at a constant speed. On the other hand, in the case of moving the moving mirror 241 in a direction of departing from the beam splitter 242, the movement resistance Ff is generated in the direction shown in FIG. 3B. Therefore, the driving voltage is adjusted so that the force Fm applied from the voice coil motor 220 becomes equal to the difference between Fs and Ff, so that the moving mirror 241 moves at a constant speed.

In cases where no foreign object is entered to the sliding portion, the force applied from the voice coil motor 220 to the movable unit 211 is required to be continuously increased or decreased in accordance with the variation of the external force Fs, but the abrupt change which occurs when a foreign object is entered does not occur. Therefore, the feedback control can be performed easily. Further, at both ends of the movable range of the moving mirror 241, it is required to perform deceleration and acceleration for switching the moving direction. However, the voltage change amount thereof is the same as that in a conventional technology, and therefore the control can be performed by feedback control similar to a conventional feedback control.

Further, even in cases where a foreign object is entered to the sliding portion of the linear guide 212 and the movable unit 211, the driving voltage of the voice coil motor 220 is raised higher than in a conventional case by the external force Fs of the coil spring 261. Therefore, it is possible to perform stable feedback control in the same manner as in the first embodiment.

With such a configuration, the external force to be applied to the movable unit 211 is determined by the spring constant of the coil spring 261. Therefore, by replacing the coil spring 261, the external force can be adjusted and the driving voltage of the voice coil motor 220 required for the movement of the moving mirror 241 at a constant speed can be adjusted.

Further, in this embodiment, the coil spring is provided so that the external force is applied to the voice coil motor side, but the coil spring may be provided so that the external force is applied toward the beam splitter side. In this case, although the polarity of the driving voltage of the voice coil motor 220 is opposite to that of this embodiment, its magnitude remains unchanged, and stable feedback control can be performed by similarly performing the control method.

In the above embodiment, the coil spring is always in an extended state, but the coil spring may be used in a state in which the coil spring is always in a compressed state. In this case, since the direction of Fs becomes opposite to that shown in FIG. 3, the direction of the driving force by the voice coil motor also becomes opposite, and its magnitude also increases as the coil spring is compressed. Although the direction and the magnitude of the external force Fs are different as described above, since the driving force can be increased by the addition of the external force, the feedback control can be stabilized.

Further, it may be configured to use both the state in which the coil spring is in an extended state and the state in which the coil spring is compressed. For example, in the configuration shown in FIG. 3, in cases where the movable unit is arranged so that the external force Fs by the coil spring becomes zero at the center of the movable range of the moving mirror, when the movable unit is moved toward the beam splitter side, the coil spring extends and the external force Fs works on the voice coil motor side. To the contrary, when the movable unit is moved toward the voice coil motor side, the coil spring is compressed, so that the external force Fs works toward the beam splitter side. In such a configuration, the external force Fs is small when the movable unit is located near the center, but the external force Fs becomes larger as the movable unit is closer to the end of the moving range. Therefore, as the movable unit approaches the end, it becomes possible to perform stable feedback control.

Further, in this embodiment, one coil spring is used, but two or more coil springs may be arranged in series or in parallel.

EXAMPLE 3

Figure 4A:
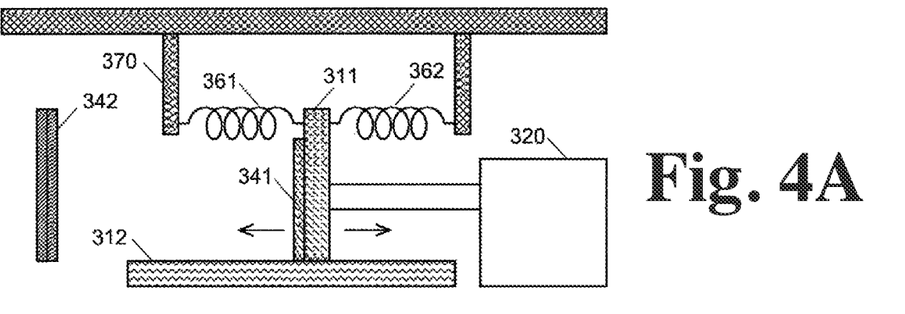
FIG. 4A is a view showing a state in which force of two coil springs are balanced, FIG.

Next, a Fourier transform type spectrophotometer according to a third embodiment of the present invention will be described with reference to FIG. 4. In the second embodiment described above, it is configured such that one coil spring is inserted between the movable unit and the elastic member fixing portion, and the external force is applied to the movable unit only in one direction. However, it may be also possible to configure such that as in this embodiment, two coil springs are inserted to apply external force in two directions with respect to the movable unit. Since the configurations are the same as those of the second embodiment except that there are two coil springs, the last two digits of the code are allotted to the same reference numerals in the above-mentioned embodiment, and the description thereof will be omitted arbitrarily.

The operation of this embodiment will be described with reference to FIG. 4. As the first and second coil springs 361 and 362, springs having the same spring constant and length are used. In addition, the first and second coil springs 361 and 362 are set so that both of them are always extended in the entire range in which the moving mirror moves. When the position of the moving mirror 341 is in the middle of the movement range, the external force Fs1 and the external force Fs2 applied to the movable unit 311 by the first and second coil springs 361 and 362 are adjusted to be equal to each other.

Figure 4B:
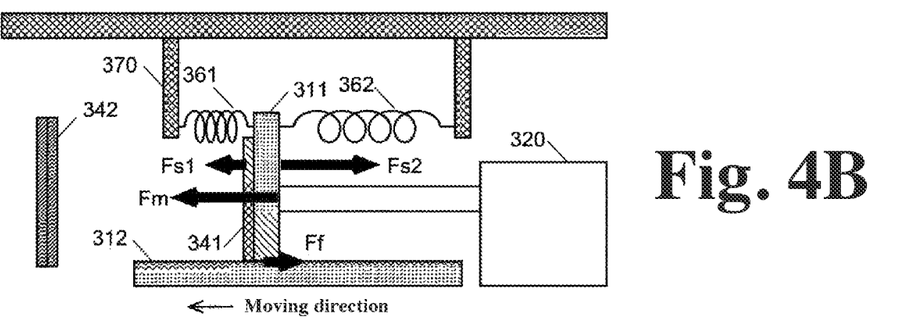

In the case of moving the moving mirror 341 in the direction approaching the beam splitter 342, as shown in FIG. 4B, the extension of the second coil spring 362 increases and the extension of the first coil spring 361 decreases so that Fs1 is smaller than Fs2 (Fs1<Fs2). Therefore, the driving voltage is adjusted so that the force Fm by the voice coil motor 320 becomes Fs2−Fs1+Ff(Fm=Fs2−Fs1+Ff), so that the moving mirror can be moved at a constant speed. At this time, the external force Fs2 from the second coil spring 362 becomes larger as the moving mirror 341 approaches the beam splitter 342, and, to the contrary, the external force Fs1 from the first coil spring 361 becomes smaller. Therefore, it is necessary to gradually raise the driving voltage of the voice coil motor 320. Since the changes of these external force Fs2 and external force Fs1 gradually change according to the moving distance, stable control can be performed by the feedback control.

Figure 4C:
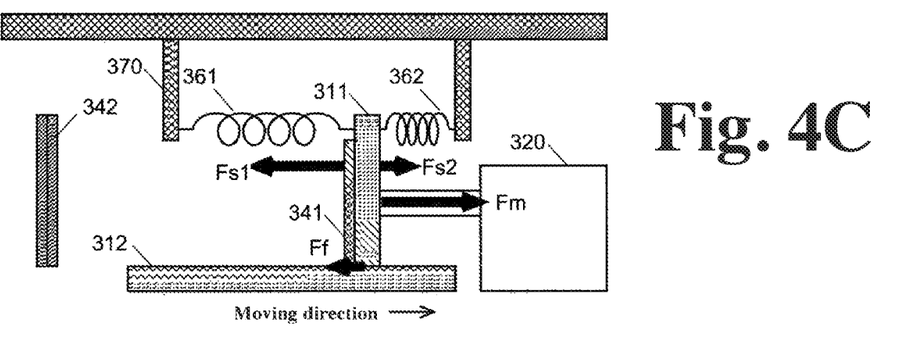
FIG. 4C is a view showing a state in which a first coil spring is extended.

In the case of moving the moving mirror 341 in a direction departing from the beam splitter 342, in contrast to the above, the external force Fs1 gradually becomes larger (FIG. 4C). Therefore, although the direction is different as compared with the case in which it approaches the beam splitter 342 described above, since the amount of change is similar, it can be easily controlled with the same control method as described above.

Therefore, also in this embodiment, external force can be applied in advance to the moving mirror 341 to raise the driving voltage of the voice coil motor. Therefore, even in cases where a foreign object is entered to the sliding portion, it is possible to stabilize the feedback control.

In this embodiment, although the first and second coil springs are always in a extended state, they may always be in a compressed state. In this case, the direction of the external force Fs1 and the direction of the external force Fs2 are opposite to that shown in FIG. 4, and its magnitude becomes large enough that the coil spring is compressed. Although the direction and magnitude of the external force Fs1 and Fs2 are different as described above, since the driving force can be increased by the addition of the external force, the feedback control can be stabilized.

Further, it may be configured to use both the state in which the coil spring is in an extended state and the state in which the coil spring is compressed. For example, in the configuration shown in FIG. 4, in cases where the movable unit is arranged so that the external force Fs1 and Fs2 by the first and second coil springs becomes zero at the center of the movable range of the moving mirror, when the movable unit is moved toward the voice coil motor side, both the external force Fs1 and Fs2 works toward the beam splitter side. To the contrary, when the movable unit is moved toward the beam splitter side, both the external force Fs1 and Fs2 works toward the voice coil motor side. Therefore, when the movable unit is located near the center, the external force Fs is small, but the magnitude of the resultant force of Fs1 and Fs2 becomes larger as it is closer to the end of the moving range, and stable feedback control can be performed.

Further, in this embodiment, the first and second coil springs are the same in length and spring constant, but the first and second coil springs different in length and spring constant may be used. In this case, since the external force Fs1 and Fs2 are different in magnitude, and therefore the required driving voltage differs depending on the moving direction of the moving mirror. However, since the voltage changes continuously in the same manner as in the aforementioned embodiment, stable control can be performed. Further, in this embodiment, although one coil spring is inserted on both sides of the movable member, two or more coil springs may be used.

EXAMPLE 4

Figure 5A:
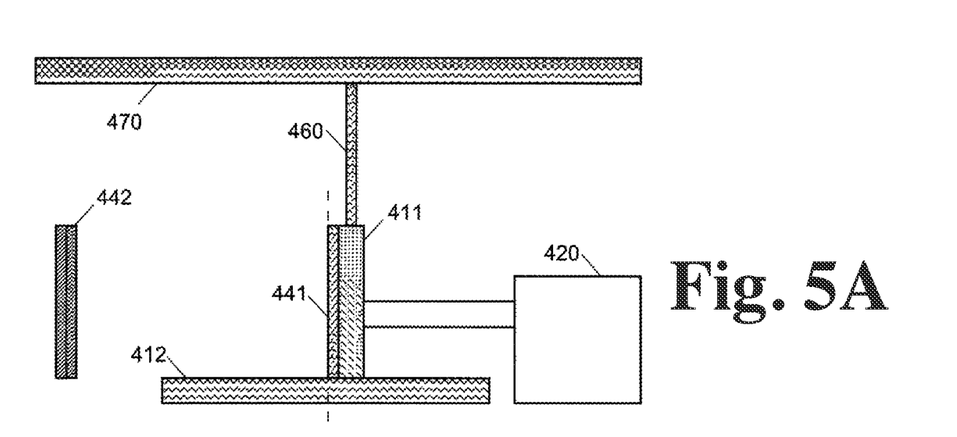
FIG. 5A is a view showing a state in which a moving mirror is at a movement center.

Next, a Fourier transform type spectrophotometer according to a fourth embodiment of the present invention will be described with reference to FIG. 5. In this embodiment, as shown in FIG. 5A, the leaf spring 460 is inserted between a movable unit 411 and an elastic member fixing portion 470. Since other configurations are the same as those in the third embodiment, the last two digits of the reference numeral are allotted to the same reference numeral in the above embodiment, and the description thereof will be omitted as appropriate.

Figure 5B:
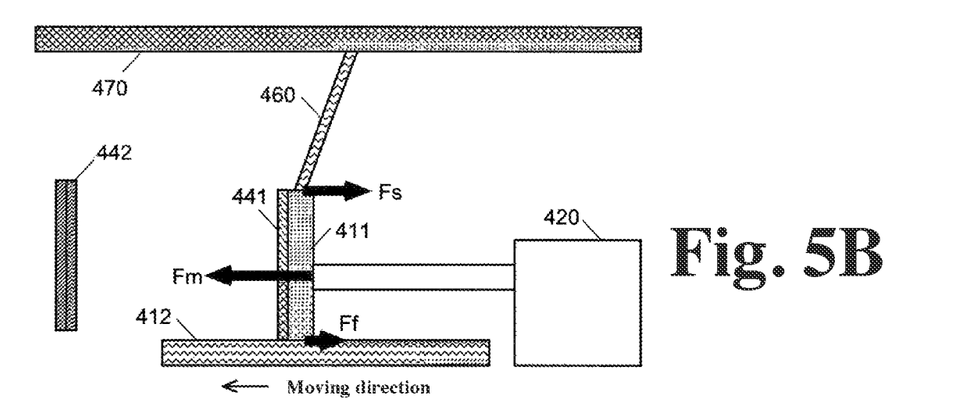
FIG. 5B is a view showing a state in which the moving mirror has moved toward a beam splitter side.
Figure 5C:
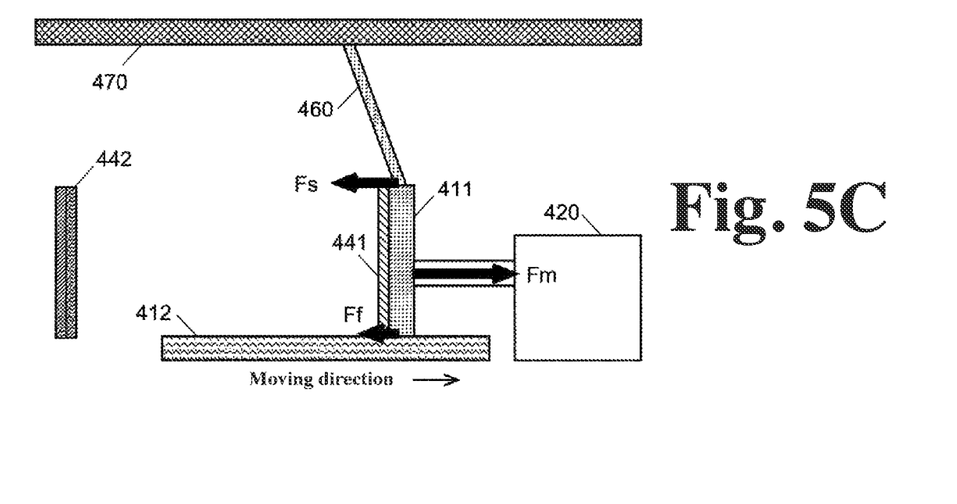
FIG. 5C is a view showing a state in which the moving mirror has moved toward a voice coil motor side.

In this embodiment, in the same manner as in the third embodiment, the external force Fs from the leaf spring 460 gradually increases according to the moving distance of the moving mirror 441 from the center of the movable range. In the case of moving the moving mirror in the direction approaching the beam splitter, as shown in FIG. 5B, the external force Fs by the leaf spring 460 is generated in a direction opposite to the traveling direction. In the case of moving the moving mirror 441 in a direction departing from the beam splitter 442, the external force Fs due to the leaf spring 460 is generated in a direction opposite to the traveling direction (FIG. 5C). Therefore, the driving voltage is adjusted so that the force Fm applied from the voice coil motor 420 becomes equal to Fs+Ff(Fm=Fs+Ff), so that the moving mirror 441 can be moved at a constant speed.

In this embodiment, since large force is required from the voice coil motor 420 by the external force Fs due to the leaf spring 460 as compared with a conventional technology, the driving voltage of the voice coil motor 420 becomes larger than that of the configuration of a conventional technology. Therefore, even in cases where a foreign object is entered to the sliding portion, it is possible to stabilize the feedback control.

In this embodiment, the external force to be applied to the movable unit 411 is determined by the spring constant of the leaf spring 460. Therefore, the leaf spring 460 is replaced to thereby adjust the external force Fs, so that the driving voltage of the voice coil motor 420 required for the movement of the moving mirror 441 at a constant speed can be adjusted.

The aforementioned embodiment is an example, and it is apparent that appropriate changes and modifications can be made along the spirit of the present invention. For example, in the aforementioned embodiment, the voice coil motor is used as the driving source for moving the moving mirror, but it can also be moved by other motors, hydraulic devices, etc. Although a coil spring and a leaf spring are used in the second to fourth embodiments, similar effects can be obtained by using other elastic members such as rubber. Although an infrared light source is used as a light source, a light source having a wavelength such as visible light or ultraviolet light can also be used.

DESCRIPTION OF REFERENCE SYMBOLS

100: Fourier transform infrared spectrophotometer
110, 510: linear motion mechanism
    111, 211, 311, 411: movable unit
    112, 212, 312, 412: linear guide
120, 220, 320, 420, 520: voice coil motor
130, 230, 530: control device
    131, 231: driving force control unit
132: speed measurement unit
140: main interferometer
    141, 241, 341, 441, 541: moving mirror
    142, 242, 342, 542: beam splitter
    143, 543: infrared light source
    144, 544: fixed mirror
    145: sample chamber
    146, 546: infrared light detector
    147: analysis device
150: laser interferometer
    151, 551: laser light source
    152, 552: laser light detector
160: inclination giving portion
261, 361, 362: coil spring
460: leaf spring
270, 370, 470: elastic member fixing portion

The invention claimed is:

1. A Fourier transform type spectrophotometer comprising:
a linear guide along which a moving mirror is movable;
a movable unit to which the moving mirror is fixed, the movable unit being movable on the linear guide;
an elastic member configured to always apply external force to the movable unit in a direction along the linear guide, wherein the external force is larger than movement resistance on the linear guide of the movable unit;
a driving source configured to apply positive or negative driving force along a moving direction of the movable unit to the movable unit; and
a controller configured to measure a moving speed of the movable unit and control the driving force of the driving source so that the movable unit is moved in a predetermined manner based on the moving speed.

2. The Fourier transform type spectrophotometer as recited in claim 1, wherein the elastic member is rubber.

3. The Fourier transform type spectrophotometer as recited in claim 1, wherein the driving source is a voice coil motor or a hydraulic device.

4. The Fourier transform type spectrophotometer as recited in claim 1, wherein the external force is larger than twice the movement resistance of the movable unit.

5. The Fourier transform type spectrophotometer as recited in claim 1, wherein the elastic member is a spring.

6. A Fourier transform type spectrophotometer, comprising:
a linear guide along which a moving mirror is movable;
a movable unit to which the moving mirror is fixed, the movable unit being movable on the linear guide;
an inclination providing structure having a first part and a second part spaced part from the first part in a horizontal direction, the first part having a vertical height higher than a vertical height of the second part, wherein the inclination providing structure is configured to incline the linear guide such that component force of gravity of the movable unit in a direction along the linear guide is greater than movement resistance on the linear guide of the movable unit;
a driving source configured to apply positive or negative driving force along a moving direction of the movable unit on the linear guide to the movable unit; and
a controller configured to measure a moving speed of the movable unit and control the driving force of the driving source so that the movable unit is moved on the linear guide in a predetermined manner based on the moving speed.

7. The Fourier transform type spectrophotometer as recited in claim 6, wherein the driving source is a voice coil motor or a hydraulic device.

\* \* \* \* \*